US005741337A

United States Patent [19]
Bone et al.

[11] Patent Number: 5,741,337
[45] Date of Patent: Apr. 21, 1998

[54] PROCESS FOR THE OXIDATIVE DYEING OF KERATINOUS FIBRES WITH A COMPOSITION WHICH CONTAINS AN OXIDATION DYE PRECURSOR, A COUPLER, AND AN OXIDANT AT AN ACIDIC PH

[75] Inventors: Eric Bone, Clichy; Roland de la Mettrie, Le Vesinet, both of France

[73] Assignee: L'Oreal, France

[21] Appl. No.: 643,498

[22] Filed: May 6, 1996

Related U.S. Application Data

[63] Continuation of Ser. No. 437,800, May 9, 1995, abandoned.

[30] Foreign Application Priority Data

May 9, 1994 [FR] France ................... 94 05688

[51] Int. Cl.⁶ ........................................ A61K 7/13
[52] U.S. Cl. .................. 8/412; 8/407; 8/410; 8/416; 8/421; 8/424
[58] Field of Search ................. 8/406, 407, 408, 8/410, 412, 416, 424, 435

[56] References Cited

U.S. PATENT DOCUMENTS

| | | | |
|---|---|---|---|
| 3,694,138 | 9/1972 | Kolapissis et al. | 8/412 |
| 3,920,384 | 11/1975 | Feinland et al. | 8/410 |
| 3,970,423 | 7/1976 | Brody et al. | 8/10.2 |
| 4,432,769 | 2/1984 | Bugaut et al. | 8/407 |
| 4,888,025 | 12/1989 | Bugaut et al. | 8/412 |
| 5,032,138 | 7/1991 | Wolfram et al. | 8/412 |
| 5,114,429 | 5/1992 | Junino et al. | 8/410 |
| 5,137,538 | 8/1992 | Madrange et al. | 8/410 |
| 5,167,669 | 12/1992 | Grollien | 8/410 |
| 5,279,619 | 1/1994 | Cotteret et al. | 8/412 |
| 5,344,464 | 9/1994 | Madrange et al. | 8/410 |
| 5,391,206 | 2/1995 | Cotteret | 8/412 |

FOREIGN PATENT DOCUMENTS

| | | |
|---|---|---|
| 0039806 | 11/1981 | European Pat. Off. . |
| 0055386 | 7/1982 | European Pat. Off. . |
| 0358550 | 3/1990 | European Pat. Off. . |
| 0360644 | 3/1990 | European Pat. Off. . |
| 2156527 | 6/1973 | France . |
| 4301663 | 2/1994 | Germany . |
| 2018836 | 10/1979 | United Kingdom . |

*Primary Examiner*—Douglas J. McGinty
*Assistant Examiner*—Caroline L. Dusheck
*Attorney, Agent, or Firm*—Finnegan, Henderson, Farabow, Garrett & Dunner, L.L.P.

[57] ABSTRACT

A composition for the oxidation dyeing of keratinous fibres, especially human hair, which comprises an oxidation dye precursor in combination with a coupler and an oxidizing agent, in an acidic medium. The composition is applied to keratinous fibers in a hair dyeing process.

34 Claims, No Drawings

PROCESS FOR THE OXIDATIVE DYEING OF KERATINOUS FIBRES WITH A COMPOSITION WHICH CONTAINS AN OXIDATION DYE PRECURSOR, A COUPLER, AND AN OXIDANT AT AN ACIDIC PH

This application is a continuation of application Ser. No. 08/437,800 filed May 9, 1995, now abandoned.

The present invention is directed to compositions for the oxidation dyeing of keratinous fibres, and especially human keratinous fibres such as hair, which employ an oxidation dye precursor in combination with a coupler and an oxidizing agent, in an acidic medium, and to a dyeing process which uses these compositions.

These compositions are intended in particular for dyeing grey or white hair which has a tendency to yellow.

It is known to dye keratinous fibres, and in particular human hair, with dyeing compositions containing oxidation dye precursors, in particular ortho- or para-phenylenediamines or ortho- or para-aminophenols, which are generally referred to as oxidation bases. Oxidation dye precursors, or oxidation bases, are colourless or slightly coloured compounds which, when mixed with oxidizing products at the time of use, are able, by a process of oxidative condensation, to give rise to coloured compounds and dyes.

It is also known that it is possible to vary the shades obtained with these oxidation bases by combining them with couplers or dye modifiers, chosen in particular from aromatic meta-diamines, meta-aminophenols and meta-diphenols.

In the particular case of the dyeing of grey or white hair, more particularly in order to remedy the yellowing thereof, while leaving it with a slight silvery or steely glint, it is possible to employ several types of products.

First of all there are shampoos based on direct dyes which are present in small quantities. Direct dyes are employed without an oxidizing agent and are capable of modifying the natural colouring of the hair more or less strongly. However, although these shampoos give an immediate effect, they have the drawback of giving a result which disappears between two shampooings.

There are also dye products which are presented in the form of a mousse or solution containing direct dyes which are applied to the hair for short waiting times. However, such products impart selective colorations to the hair; in other words, they give different shades on sensitized or nonsensitized hair. Moreover, these dyes have inadequate covering power of the hair and disappear rapidly after several shampooings.

Finally, in the field of conventional oxidation dyeing, the formulation of true grey shades is very limited and is carried out by employing dyeing processes involving relatively long waiting times, resulting in high selectivity and a dyeing result which lacks a natural appearance. Moreover, oxidation dyeing processes are generally carried out at an alkaline pH, employing strong basifying agents such as aqueous ammonia, the effect of which is to damage the keratinous fibres. With the aim of solving these various problems, the inventors have developed the dyeing composition of the invention.

The inventors have recently discovered that the use of certain oxidation dye precursors in combination with certain couplers and an oxidizing agent, in an acidic medium, makes it possible to obtain a dyeing composition which enables the above problems to be solved and which lead, after a short waiting time, to natural grey shades which are of low selectivity, of good covering power and which remedy the yellowing of grey hair and which, moreover, are persistent with regard to the action of perspiration, shampoos, chemical treatments or atmospheric agents such as light.

A subject of the present invention is therefore a composition for the oxidation dyeing of keratinous fibres, especially human keratinous fibres such as hair, which is prepared at the time of use by mixing a composition (A) and a composition (B), wherein the composition (A) comprises, in a medium appropriate for dyeing, at least one oxidation dye precursor, also called an "oxidation base," of formula (I):

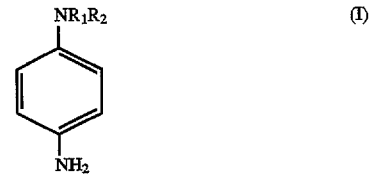

in which:

$R_1$ represents a hydrogen atom or a $C_2$–$C_6$ mono- or polyhydroxyalkyl radical;

$R_2$ represents a $C_2$–$C_6$ mono- or polyhydroxyalkyl radical, β-aminoethyl or a group of formula (II):

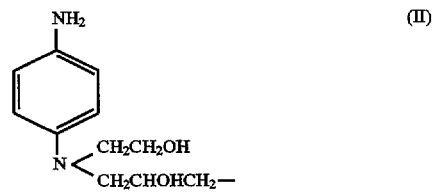

or at least one of the cosmetically acceptable salts of a compound of formula (I); and at least one coupler selected from meta-aminophenol, 2-methyl-5-aminophenol, meta-diphenol, 2-methyl-1,3-dihydroxybenzene or at least one cosmetically acceptable salt of the at least one coupler;

wherein composition (B) comprises, in a medium appropriate for dyeing, at least one oxidizing agent; and further wherein the pH of the composition which results from the mixing of composition (A) with composition (B) in a ratio by weight which ranges from 0.5:1 to 5:1, is from 2 to less than 7.

The invention also relates to a process for the oxidation dyeing of keratinous fibres which uses this composition.

The invention additionally relates to a composition for the oxidation dyeing of keratinous fibres, which comprises a composition (A) and a composition (B), wherein composition (A) comprises, in a medium appropriate for dyeing, at least one oxidation dye precursor of formula (I):

in which:

$R_1$ represents a hydrogen atom or a $C_2$–$C_6$ mono- or polyhydroxyalkyl radical;

$R_2$ represents a $C_2$–$C_6$ mono- or polyhydroxyalkyl radical, β-aminoethyl or a group of formula (II):

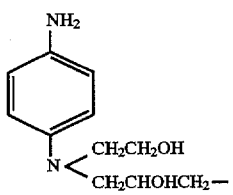

(II)

wherein composition (B) comprises, in a medium appropriate for dyeing, at least one oxidizing agent, wherein the pH of said dyeing composition is from 2 to less than 7, and further wherein the ratio by weight of composition (A) to composition (B) ranges from 0.5:1 to 5:1.

In the compositions of the invention, the salts of the compounds of formula (I) and of the couplers are preferably chosen from hydrochlorides, hydrobromides, sulphates and tartrates.

Among the $C_2$–$C_6$ mono- or polyhydroxyalkyl radicals defined for $R_1$ and $R_2$, preference is given to the β-hydroxyethyl and β,γ-dihydroxypropyl radicals.

Compounds of formula (I) which may be preferably mentioned are:
N,N-bis(β-hydroxyethyl)amino-para-phenylenediamine,
1-amino-4-(N-β-hydroxyethyl-N-β-aminoethyl) aminobenzene,
N,N'-bis(β-hydroxyethyl)-N,N'-bis(4'-aminophenyl-1,3-diamino-2-propanol,
and the cosmetically acceptable salts thereof.

The oxidizing agent is chosen from the oxidizing agents which are conventionally used in oxidation dyeing, and preferably from hydrogen peroxide, urea peroxide, alkali metal bromates, and persalts, such as perborates and persulphates. Hydrogen peroxide is particularly preferred.

The pH of the composition resulting from the mixing, at the time of use, of components (A) and (B) has a value which is preferably less than 7, and more preferably ranges from 3 to less than 7.

The pH of composition (A), as defined above, preferably ranges from 3 to 11, and may be adjusted to the desired value by using basifying agents which are commonly used in the dyeing of keratinous fibres, such as aqueous ammonia, alkali metal carbonates, alkanolamines such as mono-, di- and triethanolamines and derivatives thereof, or by using conventional acidifying agents, such as inorganic or organic acids, for instance hydrochloric acid, ortho-phosphoric acid, carboxylic acids such as tartaric acid, citric acid and lactic acid, and sulphonic acids.

The pH of composition (B) as defined above, is preferably less than 7. This pH may preferably have a minimum value of 1 and is preferably less than 5. This component may be acidified using the same kind of acidifying agents as those used for composition (A).

The oxidation precursor of formula (I) is present in a portion which preferably ranges from 0.01% to 4% by weight, approximately, relative to the total weight of the resulting composition, and which even more preferably ranges from 0.1% to 2% by weight.

The couplers of the invention, namely meta-aminophenol, 2-methyl-5-aminophenol, meta-diphenol, 2-methyl-1,3-dihydroxybenzene or their salts are present in proportions which preferably range from 0.005% to 5% by weight, approximately, relative to the total weight of the resulting composition, and even more preferably range from 0.01% to 3.5% by weight.

The composition (A) defined above may also contain, secondarily and in addition to the dye precursors of formula (I), other oxidation dye precursors of the para or ortho type and/or other couplers which are different from those defined above and/or direct dyes, so as to obtain particular colour shades.

The medium appropriate for dyeing is generally aqueous, but may also contain organic solvents in order to solubilize the compounds which would not be sufficiently soluble in water. Examples of these solvents which may preferably be mentioned are $C_1$–$C_4$ lower alkanols such as ethanol and isopropanol; glycerol; glycols and glycol ethers such as 2-butoxyethanol, propylene glycol, diethylene glycol monomethyl ether and monoethyl ether, and aromatic alcohols such as benzyl alcohol or phenoxyethanol, analogous products and mixtures thereof.

The solvents may be present in proportions which preferably range from 1 to 40% by weight relative to the total weight of the dyeing composition, and more preferably range from 5 to 30% by weight.

The compositions applied to the hair may also contain various adjuvants which are conventionally used in hair-dyeing compositions, such as anionic, cationic, nonionic, amphoteric or zwitterionic surfactants or mixtures thereof, inorganic or organic thickeners, antioxidants, penetration agents, sequestering agents, fragrances, buffers, dispersants, conditioners, film-formers, preservatives and opacifying agents.

The composition applied to the hair may be presented in various forms such as in the form of liquids, creams or gels or in any other form which is suitable for dyeing keratinous fibres and, in particular, human hair.

Another subject of the invention is a process for the oxidation of keratinous fibres and, in particular, of human keratinous fibres such as hair, using the composition as defined above.

According to this process, composition (A) is mixed at the time of use with composition (B), the weight ratio of composition (A) to composition (B) preferably varying from 0.5 to 5, and then the resulting composition being applied to the hair for a short waiting time which is preferably less than 10 minutes, and still more preferably for a waiting time which ranges from 3 to 5 minutes, approximately. The hair is then rinsed.

The weight ratio of composition (A) to composition (B) varies still more preferably from 1:1 to 3:1.

Another subject of the invention is a dyeing kit or multi-compartment device, or any other packaging system which has a plurality of compartments, of which one compartment contains the composition (A) as defined above, and a second compartment contains the composition (B) as defined above.

These devices may be equipped with a means enabling the desired mixture to be supplied to the hair, such as the devices described in Applicant's French patent application FR-2 586 913, the disclosure of which is incorporated herein by reference.

The examples which follow are intended to illustrate the invention without, however, limiting its scope.

EXAMPLES OF DYEING COMPOSITIONS

Examples 1 to 4

The following composition (A) was prepared:

| | |
|---|---|
| oleyl alcohol, polyglycerolated with 2 mol of glycerol | 4.0 g |
| oleyl alcohol, polyglycerolated with 4 mol of glycerol, containing 78% of AS | 5.7 g AS |
| oleic acid | 3.0 g |
| oleamine, ethoxylated with 2 mol of ethylene oxide, sold under the name Ethomeen O 12 by the company Akzo | 7.0 g |
| diethylaminopropyl laurylaminosuccinamate, sodium salt; containing 55% of AS | 3.0 g AS |

-continued

| | |
|---|---|
| oleyl alcohol | 5.0 g |
| oleic acid diethanolamine | 12.0 g |
| propylene glycol | 3.5 g |
| ethyl alcohol | 7.0 g |
| dipropylene glycol | 0.5 g |
| propylene glycol monomethyl ether | 9.0 g |
| sodium metabisulphite in aqueous solution containing 35 % of AS | 0.46 g As |
| ammonium acetate | 0.8 g |
| antioxidant, sequestering agent | qs |
| fragrance, preservative | qs |
| citric acid | 0.12 g |
| precursor of formula (I) | X g |
| coupler of the invention | Y g |
| other dyes | Z g |
| demineralized water | qs 100 g |

At the time of use, this composition (A) was mixed weight for weight with a composition (B) which consisted of 20-volume hydrogen peroxide 6% by weight) which had a pH of 3.

A resulting composition was obtained whose pH is indicated in the table below.

This resulting composition was applied to natural grey hair containing 90% white hairs for 5 minutes. After rinsing, washing with shampoo, rinsing and drying, the hair was dyed in the shades indicated in the table below:

| Examples in g | 1 | 2 | 3 | 4 |
|---|---|---|---|---|
| N,N'-bis(β-hydroxyethyl)-N,N'-bis(4'-aminophenyl)-1,3-diamino-2-propanol, tetrahydrochloride (precursor of formula (I)) | 0.506 | 0.253 | — | — |
| N,N-bis(β-hydroxyethyl)amino-para-phenylenediamine, sulphate (precursor of formula (I)) | — | 0.156 | — | 0.312 |
| 1-amino-4-(N-β-hydroxyethyl-N-β-aminoethyl)aminobenzene, dihydrochloride (precursor of formula (I)) | — | — | 0.40 | — |
| meta-diphenol (coupler of the invention) | — | — | 0.03 | 0.07 |
| meta-aminophenol (coupler of the invention) | 0.11 | — | — | — |
| 2-methyl-1,3-dihydroxybenzene (coupler of the invention) | — | 0.041 | — | 0.4 |
| 1-β-hydroxyethyloxy-2,4-diaminobenzene, dihydrochloride (secondary coupler) | — | — | 0.03 | — |
| 2-methyl-5-aminophenol (coupler of the invention) | — | 0.08 | 0.16 | — |
| pH of the resulting composition | 6.4 | 6.4 | 6.5 | 6.6 |
| Shade obtained | natural grey | pearly grey | silver grey | slightly pearly grey |

What is claimed is:

1. A composition for the oxidation dyeing of keratinous fibres, which comprises a mixture containing a composition (A) and a composition (B), wherein said composition (A) comprises, in a medium appropriate for dyeing, at least one oxidation dye precursor selected from compounds of formula (L):

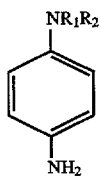

in which:

R$_1$ represents a hydrogen atom or a C$_2$–C$_6$ mono- or polyhydroxyalkyl radical;

R$_2$ represents a C$_2$–C$_6$ mono- or polyhydroxyalkyl radical, β-aminoethyl or a group of formula (II):

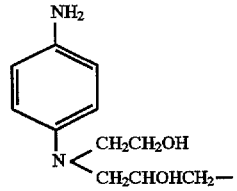

and cosmetically acceptable salts thereof; and at least one coupler selected from meta-aminophenol, 2-methyl-5-aminophenol, meta-diphenol, 2-methyl-1, 3-dihydroxybenzene and cosmetically acceptable salts thereof;

wherein said composition (B) comprises, in a medium appropriate for dyeing, at least one oxidizing agent selected from the group consisting of hydrogen peroxide, urea peroxide, alkali metal bromates and persalts;

wherein said mixture contains an amount of composition (A) relative to composition (B) in a ratio by weight which ranges from 0.5:1 to 5:1, wherein said mixture has a pH which ranges from 2 to less than 7, and wherein the components of said mixture are present in amounts effective to oxidatively dye said keratinous fibres.

2. A composition according to claim 1, wherein said salts of the compounds of formula (I) and of the couplers are selected from hydrochlorides, hydrobromides, sulphates and tartrates.

3. A composition according to claim 1, wherein said C$_2$–C$_6$ mono- or polyhydroxyalkyl radical defined for R$_1$ is a β-hydroxyethyl or β,γ-dihydroxypropyl radical.

4. A composition according to claim 1, wherein said compounds of formula (I) are selected from N,N-bis(β-hydroxyethyl) amino-para-phenylenediamine, 1-amino-4-(N-β-hydroxyethyl-N-β-aminoethyl) aminobenzene, N,N'-bis(β-hydroxyethyl)-N,N'-bis(4'-aminophenyl)-1,3-diamino-2-propanol and the cosmetically acceptable salts thereof.

5. A composition according to claim 1, wherein said persalts are selected from perborates and persulphates.

6. A composition according to claim 1, which has a pH value which ranges from 3 to less than 7.

7. A composition according to claim 1, wherein the pH of composition (A) ranges from 3 to 11.

8. A composition according to claim 1, wherein the pH of composition (B) has a value of less than 7.

9. A composition according to claim 8, wherein the pH of composition (B) ranges from 1 to less than 5.

10. A composition according to claim 1, wherein said at least one oxidation dye precursor of formula (I) is present in a proportion which ranges from 0.01% to 4% by weight relative to the total weight of the composition resulting from the mixture of composition (A) and composition (B).

11. A composition according to claim 10, wherein said at least one oxidation dye precursor of formula (I) is present in a proportion which ranges from 0.1% to 2% by weight relative to the total weight of the composition resulting from the mixture of composition (A) and composition (B).

12. A Composition according to claim 1, wherein at least one coupler compound selected from meta-aminophenol, 2-methyl-5-aminophenol, meta-diphenol, 2-methyl-1,3-dihydroxybenzene and their salts is present in a proportion which ranges from 0.005% to 5% by weight relative to the total weight of the composition resulting from the mixture of composition (A) and composition (B).

13. A composition according to claim 12, wherein said at least one coupler compound is present in a proportion which ranges from 0.01% to 3.5% by weight relative to the total weight of the composition resulting from the mixture of composition (A) and composition (B).

14. A composition according to claim 1, wherein said composition (A) further comprises at least one additional compound selected from para or ortho oxidation dye precursors or couplers which or different from those recited in claim 1, or direct dyes.

15. A composition according to claim 1, wherein said medium appropriate for dyeing consists of water or a mixture of water and a solvent selected from $C_1$–$C_4$ lower alkanols, glycerol, glycols, glycol ethers, aromatic alcohols and mixtures thereof.

16. A composition according to claim 15, wherein said solvent is present in a proportion which ranges from 1 to 40% by weight relative to the total weight of the composition resulting from the mixture of composition (A) and composition (B).

17. A composition according to claim 16, wherein said solvent is present in a proportion which ranges from 5 to 30% by weight relative to the total weight of the composition resulting from the mixture of composition (A) and composition (B).

18. A composition according to claim 1, which additionally contains at least one adjuvant selected from anionic, cationic, nonionic, amphoteric or zwitterionic surfactants or mixtures thereof, thickeners, antioxidants and any other cosmetically acceptable adjuvant.

19. A composition according to claim 1, wherein said keratinous fibres are human keratinous fibres.

20. A composition according to claim 19, wherein said human keratinous fibres are hair.

21. A composition according to claim 20, wherein said hair is grey or white hair.

22. A composition according to claim 1, wherein said composition is in the form of a liquid, a cream, a gel or any form suitable for dyeing keratinous fibres.

23. A composition according to claim 1, wherein said weight ratio ranges from 1:1 to 3:1.

24. A composition according to claim 1, wherein said $C_2$–$C_6$ mono- or polyhydroxyalkyl radical defined for $R_2$ is a β-hydroxyethyl or a β,γ-dihydroxypropyl radical.

25. A process for the oxidation dyeing of keratinous fibres, which comprises the steps of preparing a mixture containing a composition (A) and a composition (B), and immediately following said preparation, applying said mixture of composition (A) and composition (B) to said fibres, wherein said composition (A) comprises, in a medium appropriate for dyeing, at least one oxidation dye precursor selected from compounds of formula (L):

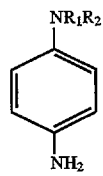

in which:
$R_1$ represents a hydrogen atom or a $C_2$–$C_6$ mono- or polyhydroxyalkyl radical;
$R_2$ represents a $C_2$–$C_6$ mono- or polyhydroxyalkyl radical, β-aminoethyl or a group of formula (LL):

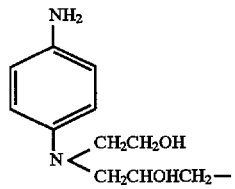

and cosmetically acceptable salts thereof; and
at least one coupler selected from meta-aminophenol, 2-methyl-5-aminophenol, meta-diphenol, 2-methyl-1,3-dihydroxybenzene and cosmetically acceptable salts thereof;

wherein said composition (B) comprises, in a medium appropriate for dyeing, at least one oxidizing agent selected from the group consisting of hydrogen peroxide, urea peroxide, alkali metal bromates and persalts;

wherein said mixture contains an amount of composition (A) relative to composition (B) in a ratio by weight which ranges from 0.5:1 to 5:1, and wherein said mixture has a pH which ranges from 2 to less than 7, wherein the components of said mixture are present in amounts effective to oxidatively dye said keratinous fibres.

26. A process according to claim 25, wherein said keratinous fibres are human keratinous fibres.

27. A process according to claim 26, wherein said human keratinous fibres are hair.

28. A process according to claim 25, wherein said compounds of formula (I) are selected from N,N-bis(β-hydroxyethyl) amino-para-phenylenediamine, 1-amino-4-(N-β-hydroxyethyl-N-γ-aminoethyl) aminobenzene, N,N'-bis(β-hydroxyethyl)-N,N'-bis(4'-aminophenyl)-1,3-diamino-2-propanol and the cosmetically acceptable salts thereof.

29. A process according to claim 25, wherein said persalts are selected from perborates and persulphates.

30. A process according to claim 25, wherein the pH of said composition which is applied to said fibres ranges from 3 to less than 7.

31. A process according to claim 25, wherein said composition is applied to said fibres with a waiting time of less than 10 minutes.

32. A process according to claim 31, wherein said composition is applied to said fibres with a waiting time which ranges from 3 to 5 minutes.

33. A process according to claim 27, wherein said hair is grey or white hair.

34. A kit for dyeing keratinous fibres, which comprises at least two compartments, one of said compartments containing a composition (A) which comprises, in a medium appropriate for dyeing, at least one oxidation dye precursor selected from compounds of formula (L):

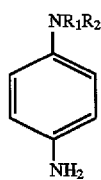

in which:

$R_1$ represents a hydrogen atom or a $C_2$–$C_6$ mono- or polyhydroxyalkyl radical;

$R_2$ represents a $C_2$–$C_6$ mono- or polyhydroxyalkyl radical, β-aminoethyl or a group of formula (LL):

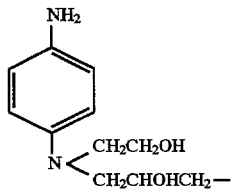

and cosmetically acceptable salts thereof; and at least one coupler selected from meta-aminophenol, 2-methyl-5-aminophenol, meta-diphenol, 2-methyl-1,3-dihydroxybenzene and cosmetically acceptable salts thereof;

and another of said compartments containing a composition (B) which comprises, in a medium appropriate for dyeing, at least one oxidizing agent selected from the group consisting of hydrogen peroxide, urea peroxide, alkali metal bromates and persalts;

wherein the amounts of the components in said compositions (A) and (B), in said compartments, is such that when said compositions (A) and (B) are combined, the resulting mixture contains an amount of composition (A) relative to composition (B) in a ratio by weight which ranges from 0.5:1 to 5:1, wherein said mixture has a pH which ranges from 2 to less than 7, and wherein the components of said mixture are present in amounts effective to oxidatively dye said keratinous fibres.

\* \* \* \* \*

UNITED STATES PATENT AND TRADEMARK OFFICE
CERTIFICATE OF CORRECTION

PATENT NO. : 5,741,337
DATED : April 21, 1998
INVENTOR(S) : Eric Bone et al.

It is certified that error appears in the above-identified patent and that said Letters Patent is hereby corrected as shown below:

Claim 1, column 5, line 67, "(L)" should read --(I)--.

Claim 12, column 7, line 4, "Composition" should read --composition--.

Claim 14, column 7, line 20, "which or" should read --which are--.

Claim 25, column 7, line 67, "(L)" should read --(I)--.

Claim 25, column 8, line 13, "(LL)" should read --(II)--.

Claim 28, column 8, line 46, "(N-B-hydroxyethyl-N-y-aminoethyl)" should read --(N-ß-hydroxyethyl-N-ß-aminoethyl)--.

Claim 34, column 8, line 67, "(L)" should read --(I)--.

Signed and Sealed this

Twenty-seventh Day of October, 1998

Attest:

BRUCE LEHMAN

*Attesting Officer*     *Commissioner of Patents and Trademarks*